US011766285B2

(12) United States Patent
Tegg et al.

(10) Patent No.: US 11,766,285 B2
(45) Date of Patent: Sep. 26, 2023

(54) CRYOGENIC ABLATION SYSTEM

(71) Applicant: St. Jude Medical, Cardiology Division, Inc., St. Paul, MN (US)

(72) Inventors: Troy T. Tegg, Elk River, MN (US); Salo Arias, Brooklyn Park, MN (US); Derek C. Sutermeister, Ham Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 529 days.

(21) Appl. No.: 16/758,797

(22) PCT Filed: Oct. 15, 2018

(86) PCT No.: PCT/US2018/055943
§ 371 (c)(1),
(2) Date: Apr. 23, 2020

(87) PCT Pub. No.: WO2019/083764
PCT Pub. Date: May 2, 2019

(65) Prior Publication Data
US 2021/0177484 A1 Jun. 17, 2021

Related U.S. Application Data

(60) Provisional application No. 62/578,325, filed on Oct. 27, 2017.

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00577* (2013.01);
(Continued)

(58) Field of Classification Search
CPC ............. A61B 2018/0212; A61B 2018/00791; A61B 2018/00744; A61B 2018/00678;
(Continued)

(56) References Cited

U.S. PATENT DOCUMENTS 3,918,439 A * 11/1975 Zimmer ................ A61B 18/02
600/128
9,414,878 B1 8/2016 Wu et al.
(Continued)

FOREIGN PATENT DOCUMENTS

| WO | 2019083765 A1 | 5/2019 |
| WO | 2019084439 A1 | 5/2019 |
| WO | 2019084442 A1 | 5/2019 |

*Primary Examiner* — Michael F Peffley
*Assistant Examiner* — Samantha M Good
(74) *Attorney, Agent, or Firm* — Armstrong Teasdale LLP

(57) ABSTRACT

The instant disclosure relates to electrophysiology catheter for tissue ablation. In particular, the instant disclosure relates to a system controller for facilitating an ablation therapy at a cryogenic ablation balloon. In an embodiment, an ablation an ablation catheter system comprising a catheter shaft including proximal and distal ends, a catheter handle coupled to a proximal end of the catheter shaft, a cryogenic ablation ballon coupled to the distal end of the catheter shaft, the ablation balloon configured and arranged to deliver a cryogenic ablation therapy to target tissue, an ablation system controller coupled to the catheter handle.

24 Claims, 6 Drawing Sheets

(52) U.S. Cl.
CPC ............... *A61B 2018/00678* (2013.01); *A61B 2018/00744* (2013.01); *A61B 2018/00791* (2013.01); *A61B 2018/0212* (2013.01)

(58) Field of Classification Search
CPC ............. A61B 2018/00577; A61B 2018/0022; A61B 18/02
See application file for complete search history.

(56) References Cited

U.S. PATENT DOCUMENTS

| | | | | |
|---|---|---|---|---|
| 2006/0129142 | A1* | 6/2006 | Reynolds | ............... A61B 18/02 607/113 |
| 2008/0027420 | A1* | 1/2008 | Wang | ..................... A61B 18/02 606/21 |
| 2008/0269737 | A1* | 10/2008 | Elmouelhi | ......... A61B 18/1477 606/41 |
| 2009/0157066 | A1 | 6/2009 | Satake | |
| 2012/0172680 | A1 | 7/2012 | Gelfand et al. | |
| 2013/0231650 | A1* | 9/2013 | Watson | ............... A61M 25/1011 606/20 |
| 2014/0378966 | A1 | 12/2014 | Haverkost et al. | |
| 2015/0157382 | A1 | 6/2015 | Avitall et al. | |
| 2016/0256214 | A9* | 9/2016 | Sharma | ................... A61B 18/04 |
| 2017/0172791 | A1* | 6/2017 | Baust | ...................... A61F 7/12 |
| 2020/0085483 | A1 | 3/2020 | Olson et al. | |
| 2020/0085484 | A1 | 3/2020 | Tegg et al. | |

* cited by examiner

A-A

CRYOGENIC ABLATION SYSTEM

CROSS-REFERENCE TO RELATED APPLICATION

This application is a National Stage Application pursuant to 35 U.S.C. § 371 and claiming priority to International Application No. PCT/US2018/055943, filed on 15 Oct. 2018, which claims the benefit of United States Provisional Application No. 62/578,325, filed 27 Oct. 2017, each of which is hereby incorporated by reference as though fully set forth herein.

BACKGROUND a. Field

The instant disclosure relates to cryogenic ablation systems, in particular systems for conducting ablation therapy within a heart, for example. In one embodiment, the instant disclosure relates to a catheter for treating cardiac arrhythmias by ablating in the vicinity of pulmonary venous tissue using a balloon filled with cryogenic fluid.

b. Background Art

The human heart routinely experiences electrical impulses traversing its many surfaces and ventricles, including the endocardial chamber. As part of each heart contraction, the heart depolarizes and repolarizes, as electrical currents spread across the heart and throughout the body. In healthy hearts, the surfaces and ventricles of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Intravascular catheters are used in a variety of diagnostic and/or therapeutic medical procedures to correct conditions such as atrial arrhythmia, including for example, ectopic atrial tachycardia, atrial fibrillation, and atrial flutter. Typically in a procedure, an intravascular catheter is manipulated through a patient's vasculature to, for example, a patient's heart, and carries one or more electrodes which may be used for mapping, ablation, diagnosis, or other treatments. Where an ablation therapy is desired to alleviate symptoms including atrial arrhythmia, an ablation catheter imparts ablative energy to cardiac tissue to create a lesion in the cardiac tissue. The lesioned tissue is less capable of conducting electrical impulses, thereby disrupting undesirable electrical pathways and limiting or preventing stray electrical impulses that may cause arrhythmias. The ablation catheter may utilize ablative energy including, for example, radio frequency (RF), cryoablation, laser, chemical, and high-intensity focused ultrasound. As is readily apparent, such an ablation treatment requires precise positioning of the ablation catheter for optimal results.

Typically, ablation therapies have been delivered by making a number of individual ablations in a controlled fashion in order to form a lesion line. Such lesion lines are often desirable around/between the pulmonary veins in the left atrium of the heart which have been associated with the introduction of erratic electric impulses into the heart. There are devices in development or being commercialized that attempt to achieve a sufficient lesion line with minimal applications of energy. Existing designs range from diagnostic catheters with a hoop and balloon mounted designs with energy applying or extracting features. The existing designs often suffer from a lack of continuous contact around a circumference of the pulmonary vein during therapy delivery, resulting in inconsistent lesion lines and incomplete electrical impulse blockage.

The foregoing discussion is intended only to illustrate the present field and should not be taken as a disavowal of claim scope.

BRIEF SUMMARY

The instant disclosure relates to electrophysiology catheter systems for tissue ablation within a cardiac muscle. In particular, the instant disclosure relates to an electrophysiology catheter system including a system controller that regulates the pressure and/or volume of cryogenic fluid that is received by an ablation balloon based on the progress of an ablation therapy on target tissue.

Aspects of the present disclosure are directed to an ablation catheter system including a catheter shaft with proximal and distal ends, a catheter handle coupled to a proximal end of the catheter shaft, a cryogenic ablation balloon coupled to the distal end of the catheter shaft, and an ablation system controller coupled to the catheter handle. The ablation balloon delivers a cryogenic ablation therapy to target tissue. The ablation system controller includes a cryogenic fluid source, and one or more manifolds in fluid communication with the cryogenic fluid source that control a flow of the cryogenic fluid to the ablation balloon. The ablation system controller further includes a servo valve located between at least one of the one or more manifolds and the ablation balloon, which regulates a pressure of the cryogenic fluid received by the ablation balloon. The controller circuitry controls the ablation therapy of the target tissue via actuation of the one or more manifolds and the servo valve. In more specific embodiments, the one or more manifolds include a tank manifold and a catheter delivery manifold. The tank manifold is positioned in line with a flow of cryogenic fluid between the cryogenic fluid source and the servo valve, and the catheter delivery manifold is positioned in line with the flow of cryogenic fluid between the servo valve and the ablation balloon.

Some embodiments of the present disclosure are directed to an ablation catheter system controller including a cryogenic fluid source, a servo valve fluidly coupled to the cryogenic fluid source, a tank manifold positioned in line with a flow of the cryogenic fluid between the cryogenic fluid source and the servo valve, and a catheter delivery manifold positioned in line with the flow of cryogenic fluid between the servo valve and the ablation balloon. The servo valve regulates a pressure of the cryogenic fluid received by an ablation balloon. The catheter and tank manifolds control a flow and pressure of the cryogenic fluid to the ablation balloon. The ablation balloon system controller further includes controller circuitry that controls the tank manifold, the catheter delivery manifold, and the servo valve to effect an ablation therapy on target tissue.

In yet other embodiments of the present disclosure, a system for controlling an ablation balloon catheter is disclosed. The system includes a cryogenic fluid source, a manifold in fluid communication with the cryogenic fluid source, a servo valve located between the manifold and the cryogenic fluid source, and controller circuitry. The manifold controls a flow of cryogenic fluid to the ablation balloon. The servo valve regulates a pressure of the cryogenic fluid received by the ablation balloon. The controller circuitry controls an ablation therapy of target tissue by the ablation balloon catheter via actuation of the manifold and the servo valve. In such embodiments, the manifold includes a normally open valve in fluid communication with the flow of cryogenic fluid to the ablation balloon and communicatively coupled to the controller circuitry, and an exhaust lumen in fluid communication between an output of the normally open valve and an atmosphere.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1A:
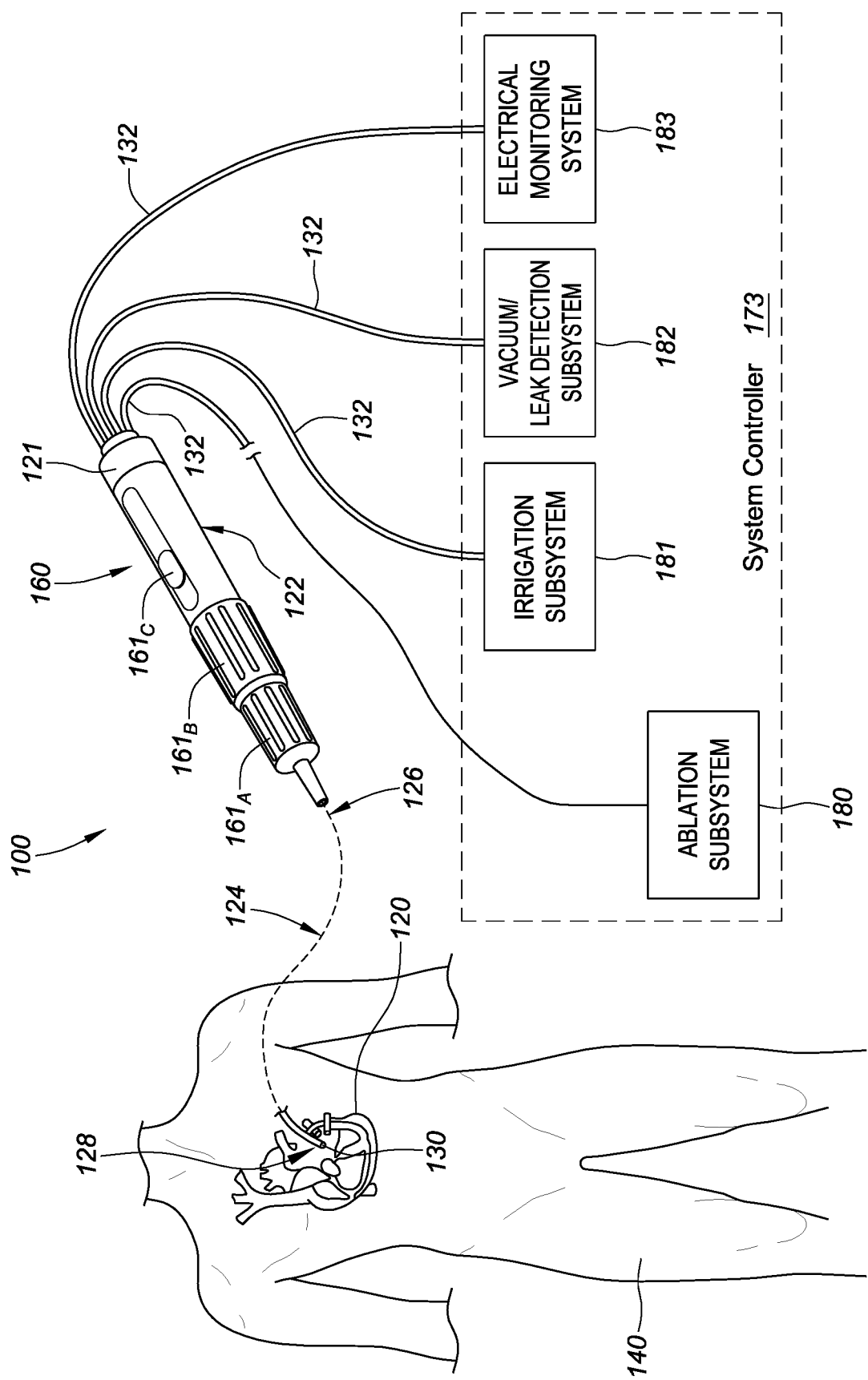
FIG. 1A is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheter systems for tissue ablation within a cardiac muscle, for example. In particular, the instant disclosure relates to a cryogenic ablation catheter system that includes an ablation balloon that receives a cryogenic fluid from a system controller for administering an ablation therapy on a pulmonary vein, for example.

Aspects of the present disclosure are directed to ablation therapies in which myocardial tissue in pulmonary veins, which form conductive pathways for electrical signals traveling through the tissue, is destroyed in order to electrically isolate sources of unwanted electrical impulses (e.g., arrhythmogenic foci) located in the pulmonary veins. The ablated myocardial tissue exhibits increased electrical resistivity which limits the flow of electrical impulses there through. By either destroying the arrhythmogenic foci, or electrically isolating them from the left atrium (via the ablated myocardial tissue), the symptoms of the arrhythmia can be reduced or eliminated.

In one example embodiment of the present disclosure, a cryogenic ablation balloon catheter may be introduced into the left atrium by a steerable catheter sheath (commonly referred to as an introducer). A catheter shaft may guide the ablation balloon once introduced into the left atrium by the sheath. Optionally, the ablation balloon catheter may include mapping electrodes at a distal end of the ablation balloon catheter. The mapping electrodes may be ring electrodes that allow the clinician to perform a pre-deployment electrical mapping of the conduction potentials of the pulmonary vein. Alternatively, mapping electrodes may be carried on-board a separate electrophysiology catheter, which may extend through a guidewire lumen that extends through a length of the ablation balloon catheter shaft. As the ablation balloon catheter contacts the pulmonary vein, mapping may be conducted using electrodes (within or adjacent to the ablation balloon) in order to verify proper location prior to deployment of the ablation balloon, as well as confirm diagnosis prior to conducting an ablation therapy.

Once a catheter sheath is in position within a patient's left atrium, a steerable ablation balloon catheter is advanced out a distal end of the sheath and toward one of four pulmonary veins. The shaft of the ablation balloon catheter may be manipulated until the distal tip of the ablation balloon catheter is substantially aligned with a longitudinal axis of the target pulmonary vein; after which, the ablation balloon is expanded and extended into contact with the target pulmonary vein. A guidewire lumen may also be used to facilitate placement of the balloon. To ablate tissue surrounding an ostia of the target pulmonary vein, a manifold distributes a super-cooled fluid (e.g., a cryogenic fluid) within the balloon—the super-cooled fluid, through conduction, cools an inner surface of the balloon in contact with the targeted tissue of the pulmonary vein to effect ablation.

Upon entering an ablation balloon, the cryogenic fluid experiences a pressure drop resulting in a phase-change from a liquid to a gas—the phase change of the cryogenic fluid absorbs thermal energy within and in conductive proximity with the balloon to ablate the myocardial tissue of the target pulmonary vein.

Details of the various embodiments of the present disclosure are described below with specific reference to the figures.

Referring now to the drawings wherein like reference numerals are used to identify similar components in the various views, FIG. 1A is a schematic and diagrammatic view of a catheter ablation system 100 for performing tissue ablation procedures. In one example embodiment, tissue 120 comprises cardiac tissue (e.g., myocardial tissue) within a human body 140. It should be understood, however, that the system may find application in connection with a variety of other tissue within human and non-human bodies, and therefore, the present disclosure is not meant to be limited to the use of the system in connection with only cardiac tissue, human bodies, and/or ablation balloons.

Catheter ablation system 100 may include a catheter 160 and an ablation subsystem 180 for controlling an ablation therapy conducted by an ablation balloon 130 at a distal end 128 of the catheter 160. The ablation subsystem 180 may control the generation and/or application of ablative energy including, in the present embodiment, cryoablation.

In the example embodiment of FIG. 1A, catheter 160 may conduct examination, diagnosis, and/or treatment of internal body tissue such as myocardial tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation balloon 130 coupled to the distal end 128 of the catheter shaft 124.

In one example application, ablation balloon 130 is manipulated through vasculature of a patient 140 using handle 122 to steer one or more portions of shaft 124 and position the ablation balloon at a desired location within tissue 120 (e.g., a cardiac muscle). In the embodiment of FIG. 1A, the ablation balloon includes one or more cryoablation manifolds that, when operated by ablation subsystem 180, ablates the tissue in contact with the ablation balloon (and in some cases tissue in proximity to the ablation balloon may be ablated by thermal transfer through the blood pool and proximal tissue).

In various specific embodiments of the present disclosure, catheter 160 may include electrophysiology electrodes and one or more positioning sensors (e.g., ring electrodes or magnetic sensors) at a distal end 128 of catheter shaft 124. In such an embodiment, the electrophysiology electrodes acquire electrophysiology data relating to cardiac tissue 120 in contact with the electrodes, while the positioning sensor(s) generate positioning data indicative of a 3-D position of the ablation balloon 130 within patient 140. In further embodiments, the catheter 160 may include other catheter components such as, for example and without limitation, steering wires and actuators, irrigation lumens and ports, pressure sensors, contact sensors, temperature sensors, additional electrodes, and corresponding conductors or leads.

Connector 121 provides mechanical and electrical connection(s) for one or more cables 132 extending, for example, from ablation subsystem 180 (through catheter handle 122 and shaft 124) to ablation balloon 130 mounted on a distal end 128 of the catheter shaft 124. The connector 121 may also provide mechanical, electrical, and/or fluid connections for cables 132 extending from other components in catheter system 100, such as, for example, irrigation subsystem 181 (when the catheter 160 is an irrigated catheter), vacuum/leak detection subsystem 182, and an electrical monitoring system 183. The vacuum/leak detection subsystem 182 may be used to both draw spent cryogenic gas from the ablation balloon 130, and to determine whether a leak has developed in an interstitial space between a dual layer balloon. The ablation subsystem 180 delivers pressurized cryogenic fluid through the connector 121 of the handle 122, with the handle 122 further routing the cryogenic fluid into a lumen that runs a length of the catheter shaft 124 and into the ablation balloon 130. The ablation subsystem 180 is discussed in more detail in reference to FIGS. 1B-4.

Handle 122 provides a location for a clinician to operate catheter 160, and may further provide steering or guidance for the shaft 124 within patient's body 140. For example, in the present embodiment, the handle includes two actuators 161$_{A-B}$ which facilitate manipulation of a distal end 128 of the shaft to steer the shaft in two perpendicularly extending planes (e.g., bi-directional steering). The handle 122 also includes a slider 161$_C$ which facilitates longitudinal manipulation of an inner shaft relative to an outer shaft (also referred to as a sheath or introducer). In other embodiments, control of the catheter may be automated by robotically driving or controlling the catheter shaft, or driving and controlling the catheter shaft using a magnetic-based guidance system. In some embodiments, the handle may include a single actuator which facilitates uni-directional manipulation of a distal end 128 of the shaft 124.

Catheter shaft 124 is an elongated, tubular, and flexible member configured for movement within a patient's body 140. The shaft supports an ablation balloon 130 at a distal end 128 of catheter 160. The shaft facilitates the transport, delivery and/or removal of fluids (including irrigation fluids, cryogenic fluids, and body fluids), medicines, and/or surgical tools or instruments. The shaft, which may be made from conventional materials used for catheters, such as polyurethane, defines one or more lumens configured to house and/or transport electrical conductors, fluids, and/or surgical tools. The catheter may be introduced into a blood vessel or other structure within the body through a conventional introducer sheath.

In one example application of a cryogenic ablation balloon catheter, consistent with the present disclosure, cardiac ablation therapy to correct for an atrial arrhythmia may be conducted. The introducer sheath is introduced through a peripheral vein (typically a femoral vein) and advanced into the right atrium. In what is referred to as a transseptal approach, the introducer sheath then makes an incision in the fossa ovalis (the tissue wall between the left and right atriums), extends through the incision in the fossa ovalis, and may be anchored thereto. The ablation catheter may then be extended through a lumen of the introducer sheath into the left atrium. Catheter shaft 124 of ablation catheter 160 may then be steered, or otherwise guided (e.g., via guidewire which extends through a guidewire lumen extending a length of the catheter shaft 124), through the left atrium to position an ablation balloon 130 into a desired location within the left atrium (e.g., a pulmonary vein).

Various embodiments of the present disclosure are directed to ablation therapy of one or more pulmonary veins via cryoablation. To achieve the desired cooling within the ablation balloon 130, cryogenic fluid (also referred to as cryofluid, cryo, or cryogen) delivered to the balloon, in response to a rapid pressure change between the manifold and the balloon, undergoes a phase change from a liquid to a gas. The phase change of the cryofluid requires a large amount of energy which has a cooling effect on tissue in proximity to the phase change. As the cryofluid expands to its gaseous state, the pressure within the balloon increases. Aspects of the present disclosure are directed to controlling the pressure within the ablation balloon 130. In some embodiments, actions may be taken to quickly alleviate pressure within the balloon; for example, dumping the head pressure and/or exhaust pressure.

Once an ablation therapy is complete, an exhaust lumen may be coupled to a vacuum to draw out any remaining fluid within the ablation balloon, thereby collapsing the ablation balloon. The ablation balloon, in its collapsed state, and catheter shaft may then be retracted back into a sheath and removed from the patient's cardiovascular system.

Various aspects of the present disclosure are directed to a system controller 173 including an ablation subsystem 180 that controls the flow of cryogenic fluid into and out of ablation balloon 130. The ablation subsystem 180 controls a flow of cryogenic fluid from a pressurized cryo-tank to the ablation balloon. In some embodiments, the ablation subsystem 180 may include a sub-cooler which uses a first portion of the cryogenic fluid to cool a radiator and a second portion of cryogenic fluid flowing there through. Also, the ablation subsystem 180 may pressure/re-pressurize the cryogenic fluid, for example, via compressor. Importantly, it has been discovered that a cryogenic fluid flow extending through a catheter shaft on its way to the ablation balloon may pre-maturely experience a phase-change where the cryogenic fluid is not maintained at a high pressure (e.g., 100 pounds per square inch ("PSI")) and/or temperature (less than room temperature—72° Fahrenheit). Accordingly, pressure and/or temperature sensor(s) may be coupled to the cryogenic fluid flow within the ablation subsystem 180, cable 132, and/or catheter shaft 124. The sensors may communicate a signal to controller circuitry (or system controller 173, or more specifically ablation subsystem 180) indicative of a pressure and/or temperature outside a threshold range, which in response to the controller circuitry may active a sub-cooler and/or compressor.

In various embodiments of the present disclosure, an ablation subsystem 180, irrigation subsystem 181, a vacuum/leak detection subsystem 182, and an electrical monitoring system 183 may be housed within a system controller 173. Though some embodiments may have one or more of these subsystems housed in self-contained unit(s).

An ablation subsystem 180 within the system controller 173 fluidly couples a cryogenic fluid source with an ablation balloon 130 via one of more manifolds and valves which are operated by controller circuitry (or system controller 173, or more specifically ablation subsystem 180). The controller circuitry may monitor a tissue ablation therapy using one or more sensors and adjust characteristics of the cryogenic fluid input to further facilitate the ablation therapy. In some embodiments, where a tissue ablation therapy exceeds safe operating limits, the manifolds and or valves may be used to quickly reduce a pressure within the system or prematurely discontinue the therapy altogether.

In various embodiments of a catheter system including an ablation balloon 130 with dual layers (also referred to as inner and outer balloons), safety features may be implemented to prevent rupture of both the inner and outer balloons which could potentially cause the distribution of cryogenic fluid (e.g., Nitrous-oxide) throughout the patient's cardiovascular system. In such embodiments, an interstitial space between the inner and outer balloons may be fluidly coupled to one or more lumens which facilitate drawing a vacuum within the interstitial space and monitoring the interstitial space for pressure changes. For example, where the inner balloon ruptures, a vacuum within the interstitial space will be reduced as cryogenic fluid enters into the interstitial space. A pressure sensor positioned within the interstitial space or the vacuum lumen would sense the change in pressure. The system controller 173, communicatively coupled to the pressure sensor, may discontinue the ablation therapy and take other corrective actions to relieve the damaged balloon 130 of residual pressure. For example, the vacuum applied to the interstitial space, via the vacuum lumen, will draw cryogen out of the ruptured, inner balloon—reducing pressure within the inner balloon.

In the present embodiment, a distal end 128 of the ablation catheter 160 includes a balloon 130 that may be delivered and inflated near a target portion of a patient's body via the cardio-vasculature system. The balloon 130 may be stored during delivery within an annulus between an inner shaft and an introducer sheath. A handle 122 of ablation catheter 160 may include rotary actuators $161_{A-B}$ which facilitate manipulation of pull wires that extend a length of the catheter shaft 124 and that are coupled to one or more pull rings near a distal end of the shaft. In response to a manipulation of the rotary actuators, the length of the catheter shaft 124 deflects, often times only in proximity to distal tip 128, which allows the shaft to be directed within a cardiovascular system. Once balloon 130 is positioned proximal to target tissue (e.g., an ostium of a pulmonary vein), the balloon may be inflated, extended into contact with the target tissue, and an ablation therapy may be conducted.

Figure 1B:
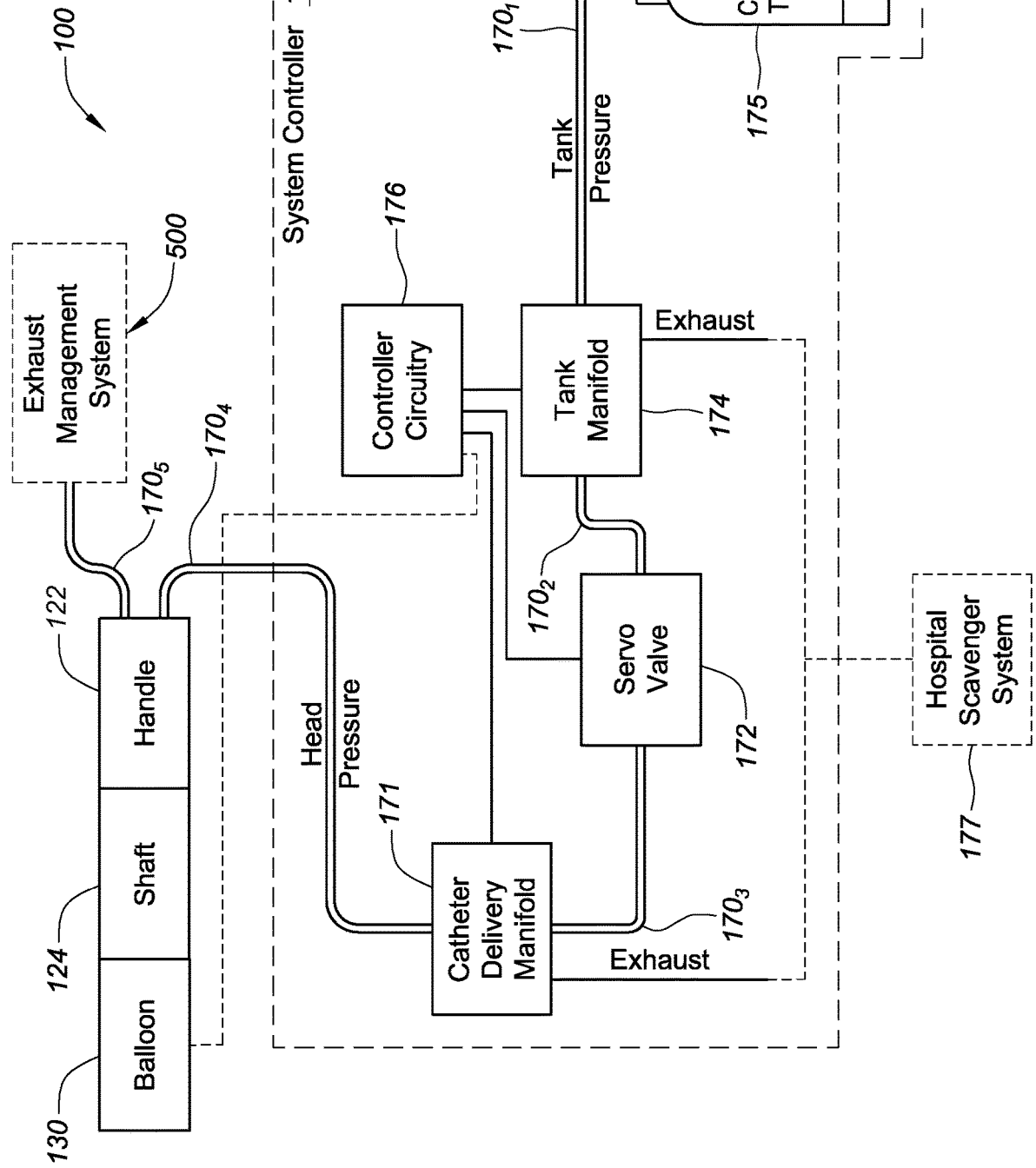
FIG. 1B is a detailed diagrammatic view of the catheter system of FIG. 1A, consistent with various aspects of the present disclosure.

FIG. 1B is a detailed diagrammatic view of the catheter system 100 of FIG. 1A, consistent with various aspects of the present disclosure.

In embodiments of the present disclosure consistent with FIG. 1B, an ablation catheter system 100 delivers cryogenic fluid between a system controller 173 and a balloon 130 at a distal end of a catheter shaft 124. Specifically, pressurized cryogenic fluid in a liquid state is delivered from a pressurized tank 175 within the system controller 173 in response to control signals received by tank manifold 174, servo valve 172, and catheter delivery manifold 171 from controller circuitry 176. The tank manifold 174 controls a flow of cryogenic fluid from the tank 175 to the servo valve 172. Upon initiation of an ablation therapy, controller circuitry 176 may initiate a purge within the tank manifold 174 which draws warmed cryogenic fluid which has been stagnate within lumen $170_1$ (and in some cases lumen $170_2$) out of the system via an exhaust lumen. In some embodiments, the exhaust lumen may be fluidly coupled with a hospital scavenger system 177 or be purged into room atmosphere. The purge replaces warmed cryogenic fluid, which may have already undergone a phase-change, with cool cryogenic fluid from the tank 175.

A servo valve 172 receives cryogenic fluid from tank 175 via tank manifold 174 and lumens $170_{1-2}$. The servo valve 172 facilitates pressure regulation from tank pressure by adjusting a cross-sectional opening through which the cryogenic fluid flows. With cryogenic tank pressure 800 PSI or higher, in some cases it may be desirable for the servo valve 172 to regulate the pressure by as much as 300 PSI (or more). For example, in some embodiments of the present disclosure, it may be desirable to deliver the cryogenic fluid to the catheter handle 122 at 500 PSI to prevent pre-mature phase-change of the cryogenic fluid to a gas before entering balloon 130. A pressure sensor downstream of the servo valve 172 (e.g., within the balloon 130, in line with lumens $170_{3-4}$, and/or at catheter delivery manifold 171) may communicate a sensed pressure with controller circuitry 176 to facilitate a control feedback loop for the servo valve 172. For example, the controller circuitry may utilize a proportional-integral-derivative controller to operate the servo valve 172, in response to pressure sensor signals indicative of tank pressure and head pressure.

In FIG. 1B, a catheter delivery manifold 171 is positioned between servo valve 172 and balloon 130. The catheter delivery manifold 171 receives a flow of cryogenic fluid from servo valve 172 and monitors a pressure and temperature thereof. For example, during a start-up procedure for catheter system 100, the catheter delivery manifold 171 may purge the cryogenic fluid lumens $170_{1-4}$ of air and/or warm cryogen by running cryogenic fluid from the tank 175 and out an exhaust lumen (and into a hospital scavenger system 177). A temperature sensor within the catheter delivery manifold 171 may sense a change in temperature associated with the presence of cryogenic fluid within the manifold. Controller circuitry 176, upon sensing the signal from the temperature sensor indicative of the change in temperature, may discontinue the purge procedure and indicate to a clinician that the ablation catheter system 100 is ready to conduct an ablation therapy.

In some embodiments, the catheter delivery manifold 171 may have two pressure sensors. A first pressure sensor may sense an incoming cryogenic fluid from servo valve 172, and a second pressure sensor may sense a head pressure of the cryogenic fluid as it exits the catheter delivery manifold 171. The controller circuitry 176 monitors the head pressure, and in response to a head pressure exceeding a threshold pressure, a valve fluidly coupled to lumen $170_4$ may be opened to exhaust some or all of the cryogenic fluid within the lumen. The second pressure sensor may also be used to sense an under-pressure event, which may cause pre-mature phase change of the cryogenic fluid within catheter shaft 124, and/or lumen $170_4$. The controller circuitry 176, in response to the under-pressure event, may command servo valve 172 to increase head pressure.

As discussed in more detail above, upon entering the balloon 130, the liquid cryogen experiences a rapid depressurization that causes a phase change of the cryogen to a gaseous state-absorbing energy and thereby ablating tissue in contact with an exterior of the balloon via conductive heat transfer. However, where the head pressure is too great, a portion of the cryogenic fluid may not experience a reduction in pressure within the balloon 130 sufficient to cause the phase-change. As a result, a portion of the cryogenic fluid may only reach the reduced pressure necessary for phase-change within an exhaust lumen extending through the catheter shaft 124 or the handle 122. Such an over-pressurization may negatively impact the efficacy of the ablation. Temperature sensors may be coupled in line with the exhaust lumen, and a substantial change in pressure from room temperature at the exhaust temperature sensors may be indicative of delayed cryogenic fluid phase-change. In yet other embodiments, pressure sensors may be utilized along the exhaust lumen to detect delayed cryogenic fluid phase change. Where the controller circuitry 176 deems the change in temperature within a safety threshold, the ablation therapy may be continued while the servo valve is actuated to decrease head pressure. Where the change in temperature exceeds a safety threshold, the controller circuitry 176 may discontinue the ablation therapy and reset the system by purging the catheter of cryogen. Where the temperature sensor(s) along the exhaust lumen does not sense a substantial temperature drop during the ablation therapy, controller circuitry may determine that the cryogenic fluid within the ablation balloon is substantially converting into a gas, as desired for ablation of tissue in contact therewith.

A gaseous state of the cryogenic fluid within balloon 130 is much less dense, with its expansion causing a flow of the cryogenic gas out of the balloon via an exhaust lumen. The exhaust lumen receives and transports the exhaust from the balloon 130, through the catheter shaft 124, to handle 122. In many embodiments, the exhaust lumen runs in parallel with a cryogenic fluid lumen. Upon arriving at the handle 122, the flow of exhaust may be run through a pressure blow-off valve. Where the pressure within the exhaust lumen, and thereby the pressure in the balloon, exceeds safe operating limits (e.g., greater than 30 PSI, or greater than 35 PSI) the pressure blow-off valve reduces the pressure therein by releasing some of the exhaust into the surrounding atmosphere to mitigate the likelihood of a rupture of the balloon 130. In some embodiments, the pressure blow-off valve may be utilized in response to a kink in the exhaust lumen between the handle 122 and system controller 173.

In some embodiments of the present disclosure, a pressure blow-off valve includes a valve ball seal, valve seal spring, and one or more vents. When a pressure of an exhaust flow within an exhaust lumen exceeds a threshold pressure, a valve seal spring of the pressure blow-off valve is overcome by the pressure exerted on a valve ball seal, and the valve ball seal releases a portion of the exhaust flow through vents within the pressure blow-off valve while the valve seal spring remains deformed. Once the pressure blow-off valve has released the excess pressure, the valve seal spring overcomes the pressure exerted on the valve ball seal to re-seal the exhaust lumen.

Where the pressure in balloon 130 is within safe operating limits, the exhaust from the balloon 130 continues to flow to the system controller 173 where the exhaust may be scavenged and re-pressurized for later use (via scavenger system 177), or released into the surrounding atmospheric environment. In yet other embodiments, the exhaust may be placed into a reservoir and disposed of at a later date.

As further shown in FIG. 1B, some embodiments of an ablation catheter system 100 may further include an exhaust management system 500 which is placed in fluid communication with an internal cavity of balloon 130 via exhaust lumen $170_5$. The exhaust management system 500, disclosed in more detail in reference to FIG. 5, receives a flow of cryogenic fluid exhaust from the balloon 130, and ultimately dispatches the exhaust to an external atmosphere or to a hospital scavenger system.

Figures 2, 2A:
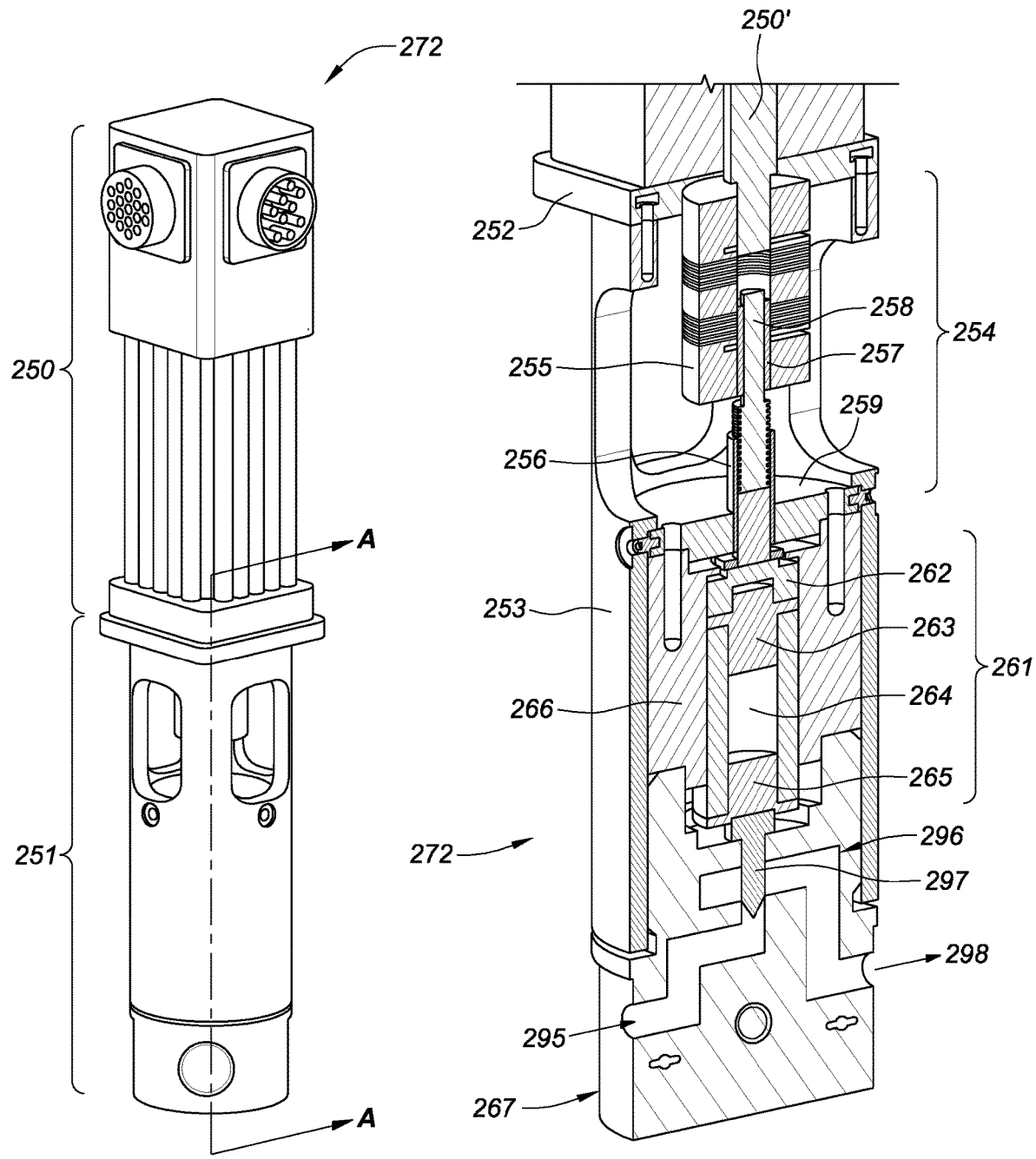
FIG. 2 is an isometric side view of a servo valve assembly, consistent with various aspects of the present disclosure.
FIG. 2A is a partial cross-sectional, isometric side view of the servo valve assembly of FIG. 2, consistent with various aspects of the present disclosure.

FIG. 2 is an isometric side view of a servo valve assembly 272, consistent with various aspects of the present disclosure. The servo valve assembly 272 includes a servo motor 250 coupled to a servo valve 251. As discussed in more detail in reference to FIG. 1B, the servo valve assembly 272 may be used within a system controller to regulate a cryogenic fluid tank pressure prior to delivery of the fluid to an ablation balloon catheter. The servo valve assembly 272 may be electronically controlled by controller circuitry which varies the valve opening to regulate the pressure in response to a clinician's commands, and feedback from one or more sensors within the ablation catheter system.

In the present embodiment, servo motor 250 is a geared servo motor which provides precise pressure control by finely controlling the size of a flow orifice there through. In some specific embodiments, the geared servo motor may have a fine pitch of approximately 1/4-80. To precisely maintain head pressure, controller circuitry may correct a driving signal to the servo motor whenever the error between the desired head pressure and actual head pressure is greater than ±3 PSI, for example.

In yet other embodiments, pressure regulation may be achieved using a pressure diaphragm with a servo air valve, or a solenoid proportion valve. However, it has been discovered that the use of solenoid proportion valve for high-pressure regulation can result in the over-heating of the valve—which may subsequently heat the cryogenic fluid flowing there through. This heating effect in the solenoid proportion valve is due to the control input for the valve being a voltage input typically between 0-24 Volts, and the desired regulation requiring the solenoid input to be near the high-end of the voltage range. For example, in one particular cryogenic fluid regulation application, in accordance with the present disclosure, a cryogenic fluid tank pressure is approximately 800 PSI and the desired regulated pressure is approximately 500 PSI. In such an application, the solenoid must receive an input signal of approximately 25 Volts to achieve a regulated pressure of 500 PSI. Depending on the length of time of an ablation therapy, the solenoid may heat-up and conductively transfer energy into the flow of cryogenic fluid. Warming the cryogenic fluid may cause premature phase-change of the cryogenic fluid prior to reaching the ablation balloon, which may impede the efficacy of the therapy. Moreover, it has further been discovered that many solenoid proportion valves suffer from a limited volumetric flow rate which may limit the heat-transfer to the ablation balloon during a therapy.

FIG. 2A is a partial cross-sectional, isometric side view of the servo valve assembly 272 of FIG. 2; specifically, a servo valve 251 portion of the assembly.

Servo motor 250 is coupled to servo valve 251 via a motor mount 252. A drive shaft 250' extends downward into the servo valve 251 and is coupled to a fine pitch lead screw 258 via a helical coupling 255. A coupling between the lead screw 258 and helical coupling 255 may be facilitated by a slip square key 257 (though other coupling means known in the art are readily envisioned). The lead screw 258 is helically coupled to a find pitch nut 256 which is rotatably coupled to a nut mount 259. As a large amount of axial force may be exerted between servo motor 250 and servo valve 251, a thrust bearing 262 may be utilized to absorb such force. The axial motion of drive assembly 254 actuates a gate within pressure regulator 267 to adjust the output pressure thereof. Inlet and outlet lumens are fluidly coupled to either side of the pressure regulator 267, with inlet and outlet connectors coupled to the respective inlet and outlet lumens on an outer surface of the servo valve 251.

A thrust bearing assembly 261, is retained within a housing 253, and includes the thrust bearing 262 which may be linearly actuated within a bore of spring spacer 266 in response to a force exerted on the thrust bearing 262 by a spring 264 and/or drive assembly 254. The spring 264 is enclosed within the spring spacer bore by proximal spring end 263 and distal spring end 265. Importantly, the thrust bearing assembly 261 prevents damage to the servo motor 250, drive assembly 254, and pressure regulator 267 by facilitating a soft contact point between the drive assembly 254 and a gate of the pressure regulator 267. Specifically, when the servo motor 250 receives a command to close the servo valve 251, the gate may seal completely, with the thrust bearing assembly 261 retracting into a bore within the spring spacer 266 to prevent damage to the drive assembly 254—where the drive assembly 254 is over extended. Upon receiving a command indicative of a desired flow of cryogenic fluid, the servo motor 250 retracts the gate, via the drive assembly 254. A flow of cryogenic fluid from the inlet 295 to the outlet 298 begins once the gate 297 is actuated to allow for a flow through cryo-lumen 296 of the pressure regulator 267. In some embodiments, the actuation of the gate 297 may be in response to a reduced pressure exerted on the bearing assembly 261 by drive assembly 254.

During initiation of an ablation catheter system, consistent with the present disclosure, the system may require the servo motor to be calibrated. In one example calibration, the servo motor would be run in reverse until arriving at a hard-stop—indicative of a home position. The servo motor may then be extended forward (e.g., 0.06"), off of the hard-stop, and the location is selected as servo home. During operation, the servo motor would be advanced to increase head pressure, and retracted to reduce head pressure—relative to servo home.

Figure 3:
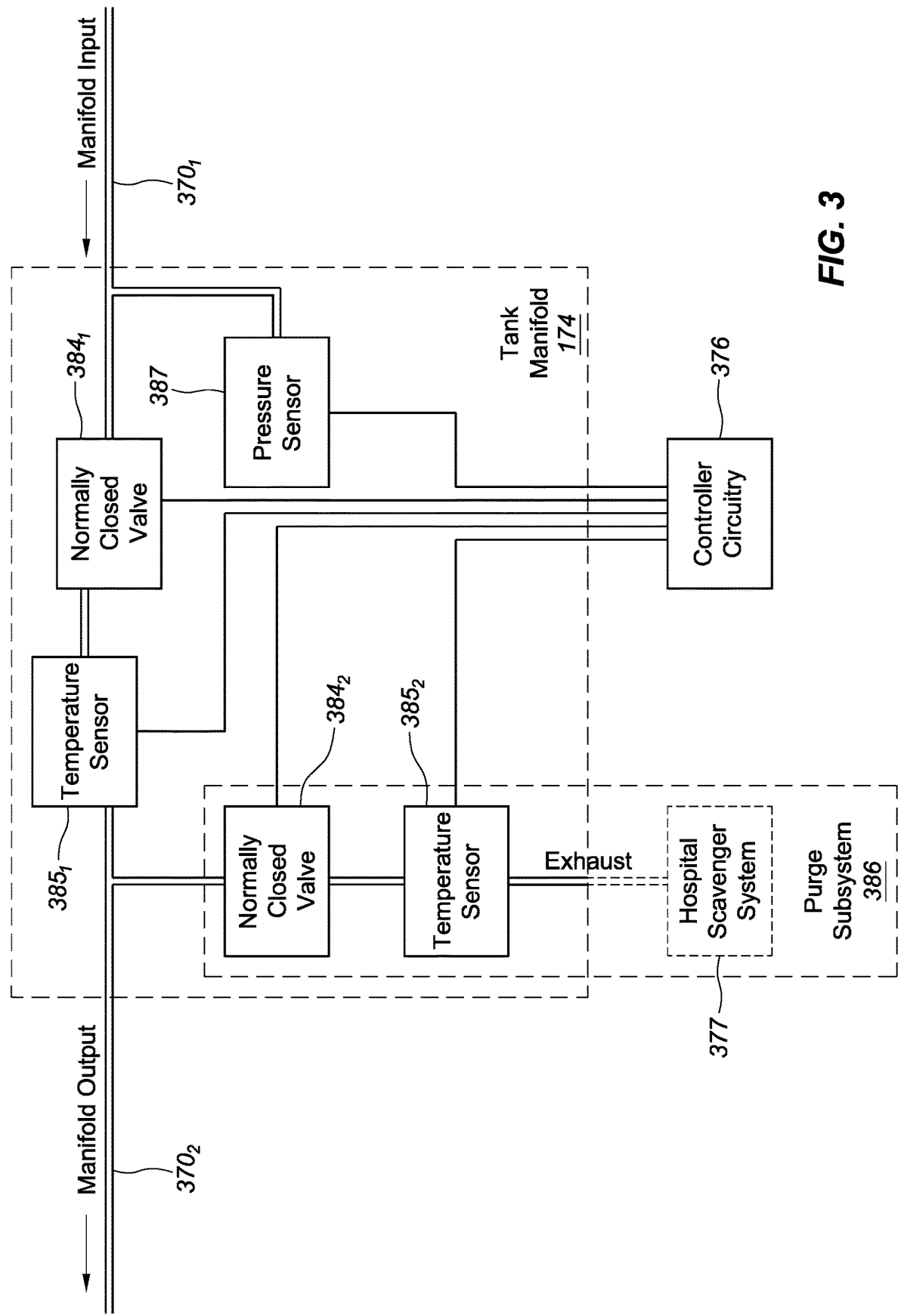
FIG. 3 is a diagrammatic view of a tank manifold of a catheter system, consistent with various aspects of the present disclosure.

FIG. 3 is a diagrammatic view of a tank manifold 174 of a catheter system, consistent with various aspects of the present disclosure. The manifold 174 receives a cryogenic fluid flow input from a cryogenic tank via lumen $370_1$, and in response to an electrical signal from controller circuitry 376 either allows the flow of cryogenic fluid through the manifold, or blocks the flow. A normally closed valve $384_1$ is positioned within the tank manifold 174 in line with a flow of cryogenic fluid through lumens $370_{1\text{-}2}$. Absent an electrical signal from controller circuitry 376, the valve inhibits the flow of fluid there through.

The tank manifold 174 also includes a pressure sensor 387 which is fluidly coupled to lumen $370_1$, upstream from the normally closed valve $384_1$. The pressure sensor 387 senses a tank pressure of the cryogenic fluid flow within lumen $370_1$. A signal from the pressure sensor 387 indicative of a tank pressure may be communicated with controller circuitry 376. The controller circuitry 376 may use the electrical signal from the pressure sensor 387 to determine a signal input for a servo valve as shown in FIG. 1B.

Due to stagnation of cryogenic fluid within the lumens 370 between ablation therapies, the cryogenic fluid within the lumens may warm and undergo a phase change. Even when the cryogenic fluid has not yet undergone a phase change, the warmed cryogenic fluid may be susceptible to phase change as it travels through a catheter shaft and experiences pressure drops. Once the cryogenic fluid undergoes a phase change, it is no longer capable of absorbing energy and thereby ablating tissue; accordingly, it may be desirable in some embodiments to purge warmed cryogenic fluid from the lumens 370. In such embodiments, the controller circuitry 376, during an initiation procedure, may sample the signal from temperature sensor $385_1$. Where the temperature sensor signal is indicative of a temperature above a threshold, the controller circuitry may initiate a purge. The tank manifold 174 includes a purge subsystem 386 which facilitates the exhausting of cryogenic fluid from the lumens 370. The purge subsystem 386 includes a normally closed valve $384_2$, and a temperature sensor $385_2$, each of which are fluidly coupled to manifold output lumen $370_2$.

To initiate a purge, controller circuitry 376 opens normally closed valves $384_{1\text{-}2}$ which facilitates a flow of cryogenic fluid out of an exhaust lumen. The exhaust lumen may be fluidly coupled to a hospital scavenger system 377. The temperature sensor $385_2$ is positioned in-line with the exhaust lumen and samples a temperature of the exhaust fluid flow. In some embodiments, the purge continues until the temperature sensor produces an electrical signal indicative of a threshold temperature or below—after which the controller circuitry may close normally closed valve $384_2$ and indicate to a clinician readiness to conduct an ablation therapy. The temperature sensor $385_1$ may also be relied-upon by the controller circuitry 376 to determine when the cryogenic fluid tank no longer contains liquid cryogen. For example, during an ablation therapy, where the electrical signal from temperature sensor $385_1$ is indicative of a warming trend, the controller circuitry may prematurely discontinue an ablation therapy and/or indicate to a clinician that the cryogenic fluid tank requires replacement. Importantly, tank pressure may not necessarily experience an appreciable drop until well after the liquid cryogen in the tank has been exhausted; accordingly, pressure sensor 387 may not provide the best indication of a level of cryogenic liquid within the tank.

Figure 4:
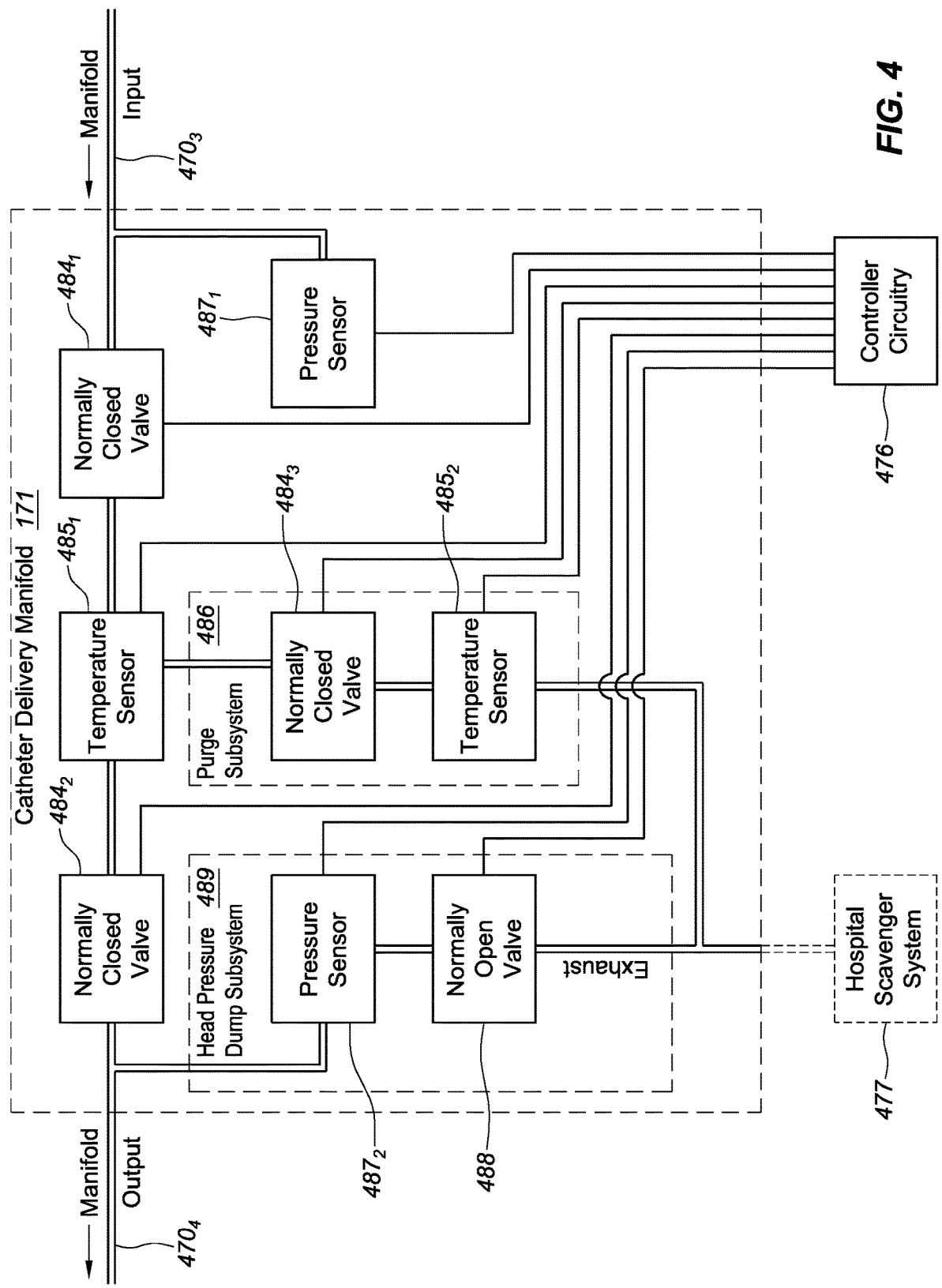
FIG. 4 is a diagrammatic view of a catheter delivery manifold of a catheter system, consistent with various aspects of the present disclosure.

FIG. 4 is a diagrammatic view of a catheter delivery manifold 171 of a catheter system, consistent with various aspects of the present disclosure. The catheter delivery manifold 171 receives a flow of cryogenic fluid from a servo valve via lumen $470_3$, and in response to an electrical signal from controller circuitry 476 either allows the flow of cryogenic fluid through the manifold, or blocks the flow. A set of normally closed valves $484_{1-2}$ are positioned within the catheter delivery manifold 171, in line with a flow of cryogenic fluid. Absent an electrical signal from controller circuitry 476, the valves inhibit the flow of fluid there through.

The catheter delivery manifold 171 also includes a pressure sensor $487_1$ which is fluidly coupled to lumen $470_3$ upstream from the normally closed valve $484_1$. The pressure sensor $487_1$ senses a regulated pressure of the cryogenic fluid flow within lumen $470_3$. A signal from the pressure sensor $487_1$, indicative of the regulated pressure, may be communicated with controller circuitry 476. The controller circuitry 476 may use the electrical signal from the pressure sensor 487, to determine a control signal error for a servo valve as shown in FIG. 1B.

As discussed in more detail above, due to stagnation within the lumens 470 between ablation therapies, cryogenic fluid within the lumens may warm and undergo a phase change; accordingly, it may be desirable in some embodiments to purge warmed cryogenic fluid from the lumens 470 before beginning an ablation therapy. In such embodiments, controller circuitry 476, during an initiation procedure, may sample the signal from temperature sensor $485_1$. Where the signal is indicative of a temperature above a threshold, the controller circuitry may initiate a purge. The catheter delivery manifold 171 includes a purge subsystem 486 which facilitates the exhausting of cryogenic fluid from lumens $470_{3-4}$, as well as lumens internal to the catheter delivery manifold. The purge subsystem 486 includes a normally closed valve $484_3$, and a temperature sensor $485_2$.

To initiate a purge, controller circuity 476 opens normally closed valves $484_{1,3}$ which facilitates a flow of cryogenic fluid out of an exhaust lumen. The exhaust lumen may be fluidly coupled to a hospital scavenger system 477. The temperature sensor $485_2$ is positioned in-line with the exhaust lumen and samples a temperature of the exhaust fluid flow. In some embodiments, the controller circuitry will purge the cryogenic fluid until the temperature sensor $485_2$ produces an electrical signal indicative of a threshold temperature or below—after which the controller circuitry may close normally closed valves $484_{1,3}$ and indicate to a clinician readiness to conduct an ablation therapy. In some specific embodiments, normally closed valve $484_2$ may be opened during a purge to flush lumen $470_4$.

During an ablation therapy, controller circuitry 476 opens normally closed valves $484_{1-2}$ allowing a flow of cryogenic fluid through the catheter delivery manifold 171. Normally closed valve $484_3$ and normally open valve 488 are closed during the ablation therapy.

In some embodiments of the present disclosure, catheter delivery manifold 171 may include a head pressure dump subsystem 489. The head pressure dump subsystem may include a pressure sensor $487_2$, and a normally open valve 488. The pressure sensor $487_2$ is fluidly coupled with lumen $470_4$, and when opened the normally open valve 488 places the lumen $470_4$ into fluid communication with an exhaust lumen. In some embodiments, the exhaust lumen is fluidly coupled with a hospital scavenger system 477.

While ablating, pressure sensor $487_2$ is fluidly coupled with lumen $470_4$, which facilitates the sensing of a head pressure of the catheter system by the pressure sensor $487_2$. The pressure sensor $487_2$ is communicatively coupled to controller circuitry 476, and during ablation therapy the controller circuitry monitors the output signal from the pressure sensor to verify that the pressure within the lumen $470_4$ remains within safe operating limits. For example, the lumen $470_4$, which extends through at least a portion of a catheter shaft, may kink in response to a steering input by a clinician. During an ablation therapy, the kink would result in the rapid over-pressurization within the lumen $470_4$—which could quickly exceed the safe operating limits of the lumen. The controller circuitry 476, in response to signals from the pressure sensor indicative of a head pressure approaching, or exceeding, safe operating limits, may actuate normally open valve 488 to alleviate some of the head pressure via the exhaust lumen.

A head pressure dump subsystem 489, while optional, may be particularly valuable due to the subsystem's ability to quickly alleviate some, or all, of the head pressure within lumen $470_4$. Absent the head pressure dump subsystem 489, an ablation catheter system would be reliant on a servo valve to reduce the head pressure, but would otherwise be incapable of exhausting the cryogenic fluid within the lumen $470_4$. Importantly, the use of the servo valve to reduce head pressure presupposes that lumen $470_4$ is still fluidly coupled to an exhaust lumen opposite the ablation balloon. However, where the lumen $470_4$ is kinked, a catheter delivery manifold 171, absent the head pressure dump subsystem 489, would be unable to relieve a pressure with the lumen—potentially leading to a failure of the ablation balloon.

In the event of a power failure within the operating suite, while an ablation therapy is in progress, normally closed valves $484_{1,3}$ will discontinue a flow of cryogenic fluid into the ablation balloon catheter, and normally open valve 488 will open to exhaust any cryogenic fluid within lumen $470_4$—thereby drawing down a head pressure to atmospheric pressure.

Figure 5:
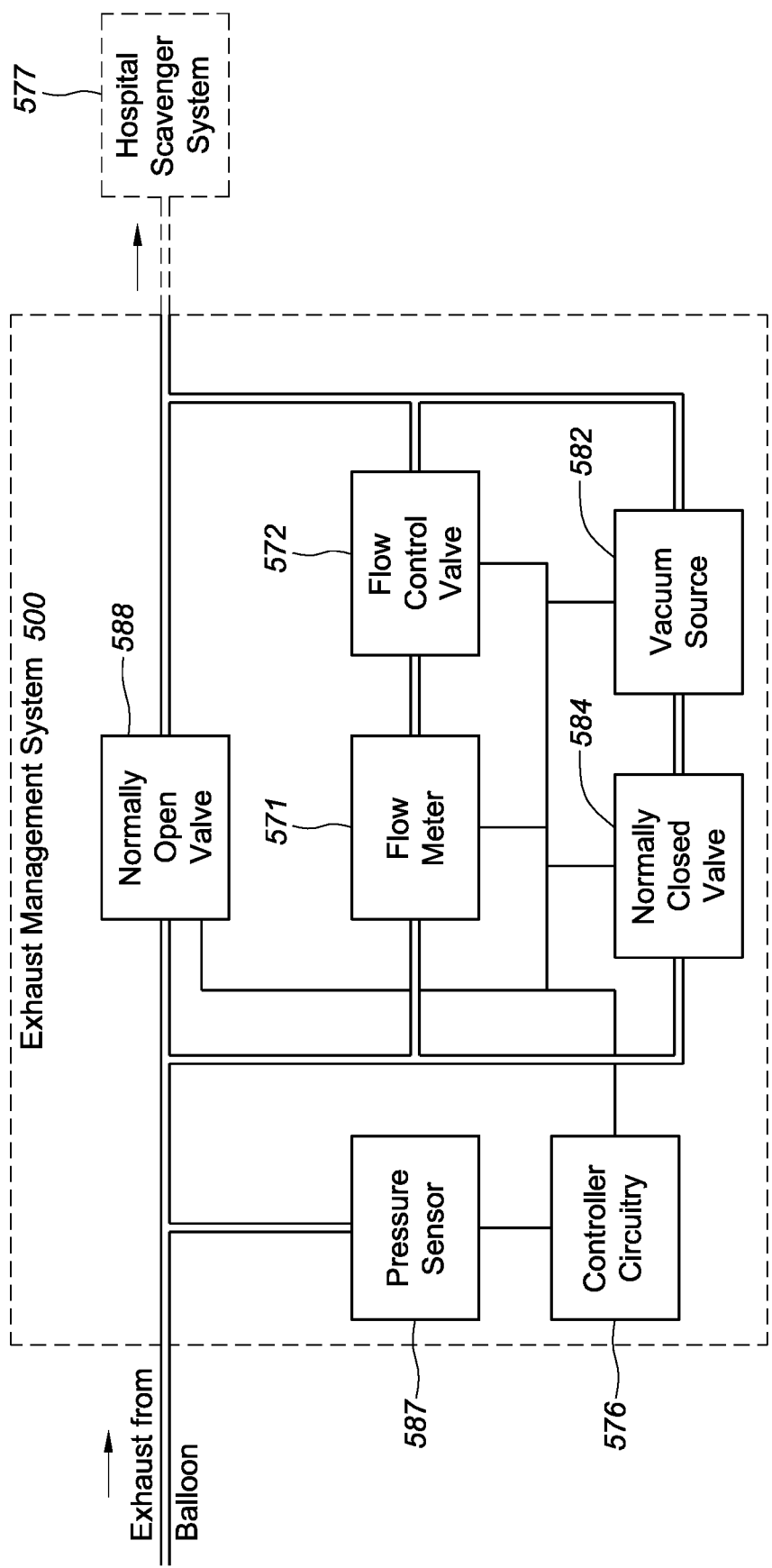
FIG. 5 is a diagrammatic view of an exhaust management system, consistent with various aspects of the present disclosure.

FIG. 5 is a diagrammatic view of an exhaust management system 500, consistent with various aspects of the present disclosure. The exhaust management system 500 receives an exhaust of cryogenic fluid from an ablation balloon, and ultimately dispatches the exhaust to an external atmosphere or to a hospital scavenger system 577. The exhaust management system 500 may include up to three different flow paths that may be operated independently of one another in response to control signals received by the various components of the flow paths from controller circuitry 576.

In some embodiments of the exhaust management system 500 of FIG. 5, a pressure sensor 587 senses a pressure of the cryogenic fluid exhaust from the ablation balloon and transmits a signal to controller circuitry 576 indicative of the pressure. Where the pressure sensed is within a threshold range, a normally open valve 588 may be maintained in an open position by the controller circuitry—allowing the flow of exhaust through exhaust management system 500 without interruption. However, in some embodiments, for example where the exhaust pressure is below a threshold range, the normally open valve 588 may be closed and a flow control valve 572 actuated. A flow meter 571 may sense a flow of exhaust through the flow control valve, with the controller circuitry 576 sampling a signal from the pressure sensor 587 and/or the flow meter 571, and actuating the flow control valve 572 in response thereto. In such a configuration, the controller circuitry 576 may precisely maintain a desired exhaust pressure that facilitates cryogenic cooling within the ablation balloon.

After completion of an ablation therapy, the ablation balloon must be deflated to facilitate retraction of the balloon back into a catheter sheath—for removal from the patient's cardiovascular system. To deflate the balloon, any remaining cryogenic fluid must be drawn out of the ablation balloon. Accordingly, controller circuitry 576 may close normally open valve 588 and flow control valve 572, open normally closed valve 584, and activate a vacuum source 582. The vacuum source 582 draws the remaining cryogenic fluid within the ablation balloon to deflate the balloon for withdrawal via the catheter sheath.

Ablation balloons have been developed for a variety of different applications and take a number of different forms. Aspects of the present disclosure may utilize ablation balloons of various types and different mechanical construction. The ablation balloons may be either of an electrically or thermally conductive material, and can be either self-erecting or mechanically erected, such as through the use of an internal balloon.

Pulmonary vein isolation balloon catheters as disclosed herein may be introduced into a patient's cardiovascular system via an introducer sheath (such as St. Jude Medical, Inc.'s Agilis™ NxT Steerable Introducer sheath).

In various embodiments of the present disclosure, an ablation balloon is capable of conducting ablation therapy at more than one location of the ablation balloon. For example, energy can be delivered to a proximal, distal, or intermediary portion of the ablation balloon. In some embodiments, the proximal, distal, intermediary portions, or combinations thereof may simultaneously conduct ablation therapy. In more specific embodiments, the amount of ablation therapy (e.g., energy transmitted to the tissue) conducted at a tissue location may be controlled individually.

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Additional information and examples can be found in U.S. provisional application No. 62/432,065, filed on 9 Dec. 2017; U.S. provisional application No. 62/578,352 filed 27 Oct. 2017; U.S. provisional application No. 62/578,201 filed 27 Oct. 2017; U.S. provisional application No. 62/578,320 filed 27 Oct. 2017, and U.S. provisional application 62/578,178 filed 27 Oct. 2017, each of which is hereby incorporated by reference as if set forth fully herein.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation catheter system comprising:
   a catheter shaft including proximal and distal ends;
   a catheter handle coupled to a proximal end of the catheter shaft;
   a cryogenic ablation balloon coupled to the distal end of the catheter shaft, the ablation balloon configured and arranged to deliver a cryogenic ablation therapy to target tissue; and
   an ablation system controller coupled to the catheter handle, the system controller including:
      a cryogenic fluid source;
      a tank manifold positioned in line and in fluid communication with the cryogenic fluid source, and configured to control a flow of the cryogenic fluid to the cryogenic ablation balloon;
      a catheter delivery manifold positioned in line with and in fluid communication with the cryogenic ablation balloon, and configured to control the flow of the cryogenic fluid to the cryogenic ablation balloon;
      a servo valve located between the tank manifold and the catheter delivery manifold, and configured and arranged to regulate a pressure of the cryogenic fluid received by the ablation balloon; and
      controller circuitry configured and arranged to control the ablation therapy of the target tissue via actuation of the tank manifold, the catheter delivery manifold, and the servo valve.

2. The ablation catheter system of claim 1, wherein the tank manifold includes a normally closed valve, a tank pressure sensor fluidly coupled upstream of the normally closed valve, and a temperature sensor fluidly coupled downstream of the normally closed valve, the tank pressure sensor configured and arranged to sense a pressure of the cryogenic fluid source and transmit an electrical signal to the controller circuitry indicative of the pressure, the temperature sensor configured and arranged to sense a temperature of the cryogenic fluid within the tank manifold and transmit another electrical signal to the controller circuitry indicative of the temperature; and
   wherein the controller circuitry is configured and arranged to:
      adjust a control signal to the servo valve in response to a change in the signal from the tank pressure sensor, and
      initiate a purge of the cryogenic fluid within the tank manifold in response to the signal from the temperature sensor indicative of a temperature exceeding a threshold temperature.

3. The ablation catheter system of claim 1, wherein the catheter delivery manifold includes a head pressure dump subsystem with a head pressure sensor fluidly coupled to an output of the catheter delivery manifold and communicatively coupled to the controller circuitry, and a normally open valve fluidly coupled between the head pressure sensor and an exhaust lumen;
   the head pressure sensor is configured and arranged to communicate a signal to the controller circuitry indicative of a pressure of the output of the catheter delivery manifold; and
   the controller circuitry is configured and arranged in response to the signal from the head pressure sensor being indicative of a pressure exceeding a threshold pressure to:
      actuate the normally open valve to an open position,
      monitor the signal from the head pressure sensor, and
      actuate the normally open valve to a closed position in response to the signal from the head pressure sensor being indicative of the threshold pressure or below.

4. The ablation catheter system of claim 1, wherein the tank manifold includes a first normally closed valve communicatively coupled to the controller circuitry, a tank pressure sensor fluidly coupled upstream of the first normally closed valve, a temperature sensor fluidly coupled downstream of the normally closed valve and communicatively coupled to the controller circuitry, and a purge subsystem including a second normally closed valve, and an exhaust lumen;
   the tank pressure sensor communicatively coupled to the controller circuitry, and configured and arranged to sense a pressure of the cryogenic fluid source and transmit an electrical signal to the controller circuitry indicative of the pressure; and
   the temperature sensor communicatively coupled to the controller circuitry, and configured and arranged to sense a temperature of the cryogenic fluid within the tank manifold and transmit another electrical signal to the controller circuitry indicative of the temperature.

5. The ablation catheter system of claim 4, wherein the controller circuitry is configured and arranged to:
   adjust a control signal to the servo valve in response to a change in the signal from the tank pressure sensor,
   initiate a purge of the cryogenic fluid within the tank manifold, in response to the signal from the temperature sensor indicative of the temperature exceeding a threshold temperature, by:
      actuating the first normally closed valve and the second normally closed valve to open positions;
      monitoring the signal from the temperature sensor; and
      actuating the first normally closed valve and the second normally closed valve to closed positions in response to the signal from the temperature sensor being indicative of the temperature being at the threshold temperature or below.

6. The ablation catheter system of claim 5, wherein the exhaust lumen is fluidly coupled to a hospital scavenger system.

7. The ablation catheter system of claim 1, further including a temperature sensor fluidly coupled to an output of the cryogenic fluid source, the temperature sensor configured and arranged to sense a temperature of the cryogenic fluid source and transmit an electrical signal to the controller circuitry indicative of the temperature at the output of the cryogenic fluid source, the controller circuitry configured and arranged to receive the electrical signal from the temperature sensor and to actuate the tank manifold and the catheter delivery manifold to closed positions in response to the sensed temperature being greater than a threshold temperature indicative of liquid cryogenic fluid.

8. The ablation catheter system of claim 1, wherein the catheter delivery manifold includes a purge subsystem and a head pressure dump subsystem.

9. The ablation catheter system of claim 8, wherein the catheter delivery manifold includes first and second normally closed valves, and a first temperature sensor fluidly coupled between the first and second normally closed valves, each of the first and second normally closed valves, and the first temperature sensor communicatively coupled to the controller circuitry.

10. The ablation catheter system of claim 8, wherein the purge subsystem includes a third normally closed valve, a second temperature sensor, and an exhaust lumen.

11. The ablation catheter system of claim 10, wherein the controller circuitry is configured and arranged to:
initiate a purge of the cryogenic fluid within the catheter delivery manifold, in response to the signal from the first temperature sensor being indicative of a temperature exceeding a threshold temperature, by:
actuating the first and third normally closed valves to open positions,
monitoring the signal from the second temperature sensor, and
actuating the first and third normally closed valves to closed positions in response to the signal from the second temperature sensor being indicative of the temperature threshold or below.

12. The ablation catheter system of claim 8, wherein the catheter delivery manifold includes a pressure sensor fluidly coupled to an output of the servo valve and communicatively coupled to the controller circuitry, the pressure sensor configured and arranged to sense a pressure of the cryogenic fluid and transmit an electrical signal to the controller circuitry indicative of the pressure, and
wherein the controller circuitry is configured and arranged to adjust a control signal to the servo valve in response to the signal received from the pressure sensor, where a target pressure minus the sensed pressure is indicative of a pressure control error.

13. The ablation catheter system of claim 8, wherein the head pressure dump subsystem includes a head pressure sensor fluidly coupled to an output of the catheter delivery manifold and communicatively coupled to the controller circuitry, and a normally open valve fluidly coupled between the head pressure sensor and an exhaust lumen.

14. The ablation catheter system of claim 13, wherein the head pressure sensor is configured and arranged to communicate a signal to the controller circuitry indicative of a pressure of the output of the catheter delivery manifold, and the controller circuitry is configured and arranged, in response to the signal from the head pressure sensor being indicative of a pressure exceeding a threshold pressure, to:
actuate the normally open valve to an open position,
monitor the signal from the head pressure sensor, and
actuate the normally open valve to a closed position in response to the signal from the head pressure sensor being indicative of the pressure threshold or below.

15. An ablation catheter system controller comprising:
a cryogenic fluid source;
a servo valve fluidly coupled to the cryogenic fluid source and configured and arranged to regulate a pressure of the cryogenic fluid received by an ablation balloon;
a tank manifold positioned in line with a flow of the cryogenic fluid between the cryogenic fluid source and the servo valve;
a catheter delivery manifold positioned in line with the flow of cryogenic fluid between the servo valve and the ablation balloon;
the catheter and tank manifolds configured and arranged to control a flow of the cryogenic fluid to the ablation balloon; and
controller circuitry configured and arranged to control the tank manifold, the catheter delivery manifold, and the servo valve to affect an ablation therapy on target tissue.

16. The ablation catheter system controller of claim 15, wherein the tank manifold includes a normally closed valve, a pressure sensor fluidly coupled upstream of the normally closed valve, and a temperature sensor fluidly coupled downstream of the normally closed valve, the pressure sensor configured and arranged to sense a pressure of the cryogenic fluid source and transmit an electrical signal to the controller circuitry indicative of the pressure, the temperature sensor configured and arranged to sense a temperature of the cryogenic fluid within the tank manifold and transmit another electrical signal to the controller circuitry indicative of the temperature; and
wherein the controller circuitry is configured and arranged to
adjust a control signal to the servo valve in response to a change in the signal from the pressure sensor, and
initiate a purge of the cryogenic fluid within the tank manifold in response to the signal from the temperature sensor indicative of a temperature exceeding a threshold temperature.

17. The ablation catheter system controller of claim 15, wherein the catheter delivery manifold includes first and second normally closed valves, and a first temperature sensor fluidly coupled between the first and second normally closed valves, each of the first and second normally closed valves, and the first temperature sensor communicatively coupled to the controller circuitry.

18. The ablation catheter system controller of claim 17, wherein the catheter delivery manifold further includes a purge subsystem with a third normally closed valve, a second temperature sensor, and an exhaust lumen.

19. The ablation catheter system controller of claim 18, wherein the controller circuitry is further configured and arranged to initiate a purge of the cryogenic fluid within the tank manifold, in response to the signal from the first temperature sensor being indicative of a temperature exceeding a threshold temperature, by
actuating the first and third normally closed valves to open positions,
monitoring the signal from the second temperature sensor, and
actuating the first and third normally closed valves to closed positions in response to the signal from the second temperature sensor being indicative of the temperature threshold or below.

20. The ablation catheter system controller of claim 18, wherein the catheter delivery manifold includes a head pressure dump subsystem with a head pressure sensor fluidly coupled to an output of the catheter delivery manifold and communicatively coupled to the controller circuitry, and a normally open valve fluidly coupled between the head pressure sensor and an exhaust lumen.

21. The ablation catheter system controller of claim 20, wherein the head pressure sensor is configured and arranged to communicate a signal to the controller circuitry indicative of a pressure of the output of the catheter delivery manifold, and the controller circuitry is configured and arranged, in response to the signal from the head pressure sensor being indicative of a pressure exceeding a threshold pressure, to actuate the normally open valve to an open position, monitor the signal from the second pressure sensor, and actuate the normally open valve to a closed position in response to the signal from the head pressure sensor being indicative of the pressure threshold or below.

22. A system for controlling an ablation balloon catheter comprising:

a cryogenic fluid source, a manifold in fluid communication with the cryogenic fluid source and configured and arranged to control a flow of cryogenic fluid to the ablation balloon, a servo valve located between the manifold and the cryogenic fluid source, and configured and arranged to regulate a pressure of the cryogenic fluid received by the ablation balloon, controller circuitry configured and arranged to control an ablation therapy of target tissue by the ablation balloon catheter via actuation of the manifold and the servo valve; and wherein the manifold includes a normally open valve in fluid communication with the flow of cryogenic fluid to the ablation balloon and communicatively coupled to the controller circuitry, and an exhaust lumen in fluid communication between an output of the normally open valve and an atmosphere.

23. The system of claim 22, further including a pressure sensor fluidly coupled to an output of the manifold and communicatively coupled to the controller circuitry, the pressure sensor configured and arranged to communicate a signal to the controller circuitry indicative of a pressure of the output of the manifold; and the controller circuitry is further configured and arranged in response to the signal from the pressure sensor being indicative of a pressure exceeding a threshold pressure to actuate the normally open valve to an open position, monitor the signal from the pressure sensor, and actuate the normally open valve to a closed position in response to the signal from the pressure sensor being indicative of a threshold pressure or below.

24. The system of claim 22, wherein the normally open valve is configured in response to a lack of signal from the controller circuitry to release the flow of cryogenic fluid to the atmosphere.

* * * * *